United States Patent
Nuvula et al.

(10) Patent No.: US 9,556,253 B2
(45) Date of Patent: Jan. 31, 2017

(54) PROCESS FOR INCREASED YIELD OF IMMUNOGLOBULIN FROM HUMAN PLASMA

(71) Applicant: HEMARUS THERAPEUTICS LIMITED, Hyderabad (IN)

(72) Inventors: Ashok Kumar Nuvula, Hyderabad (IN); Zinia Chakraborty, Hyderabad (IN); Vvs Sailesh Bavirisetti, Hyderabad (IN); Thirupati Reddy Katkuri, Hyderabad (IN); Uma Devi Komath, Hyderabad (IN)

(73) Assignee: HEMARUS THERAPEUTICS LIMITED, Hyderabad (IN)

( * ) Notice: Subject to any disclaimer, the term of this patent is extended or adjusted under 35 U.S.C. 154(b) by 0 days.

(21) Appl. No.: 14/576,261

(22) Filed: Dec. 19, 2014

(65) Prior Publication Data
US 2016/0152690 A1 Jun. 2, 2016

(30) Foreign Application Priority Data
Dec. 2, 2014 (IN) .......................... 6047/CHE/2014

(51) Int. Cl.
| | | |
|---|---|---|
| *C07K 1/18* | (2006.01) | |
| *A61K 38/00* | (2006.01) | |
| *C07K 16/06* | (2006.01) | |
| *A61K 39/00* | (2006.01) | |

(52) U.S. Cl.
CPC ............ *C07K 16/065* (2013.01); *A61K 38/00* (2013.01); *C07K 1/18* (2013.01); *A61K 2039/505* (2013.01); *C07K 2317/10* (2013.01); *C07K 2317/21* (2013.01)

(58) Field of Classification Search
None
See application file for complete search history.

(56) References Cited

U.S. PATENT DOCUMENTS

| | | |
|---|---|---|
| 6,281,336 B1 | 8/2001 | Laursen et al. |
| 6,307,028 B1 | 10/2001 | Lebing et al. |
| 2007/0049733 A1 | 3/2007 | Zurlo et al. |

FOREIGN PATENT DOCUMENTS

| | | |
|---|---|---|
| CN | 102552906 B | 11/2013 |
| CN | 102584934 B | 11/2013 |
| CN | 103554253 A | 2/2014 |
| CN | 103665100 A | 3/2014 |
| CN | 104004089 A | 8/2014 |
| EP | 0123029 A1 | 10/1984 |
| EP | 0180766 A2 | 5/1986 |
| EP | 2519540 A1 | 11/2012 |
| JP | H09249580 A | 9/1997 |
| JP | H107588 A | 1/1998 |
| JP | 2011102314 A | 5/2011 |
| WO | 9805686 A1 | 2/1998 |
| WO | WO 98/05686 * | 2/1998 |

OTHER PUBLICATIONS

Biotechnol. J., 2006, 148-163, 1.
J. Am. Chem. Soc., 1946, 459-475, 68.
Lontos, J., Chromatographic purification of immunoglobulins at CSL bioplasma; a manufacturing perspective. Plasma Product Biotech meet, http://www.bo-conf.com/ppb05/present/ppt.htm 2005.

* cited by examiner

*Primary Examiner* — Benjamin P Blumel
(74) *Attorney, Agent, or Firm* — Harita S. Achanta

(57) ABSTRACT

The present invention discloses a preparation method for large scale production of human immunoglobulins (IgG) with high yields by an improved all-chromatography process scheme that eliminates ethanol precipitation. The process of extracting immunoglobulins is such that the other therapeutic proteins in plasma are left unaffected and are available for extraction separately from the same plasma sample. The yields obtained are in the range of 7 to 8 grams of IgG per liter of plasma. The high yielding process scheme of the present invention comprises of chromatographic steps and viral inactivation or removal steps to obtain a purified immunoglobulin protein that complies with pharmacopoeial limits and is suitable for therapeutic administration (normal intravenous immunoglobulin—IVIG).

3 Claims, 7 Drawing Sheets

FIG. 1. An outline illustration of the process scheme for the purification of IgG
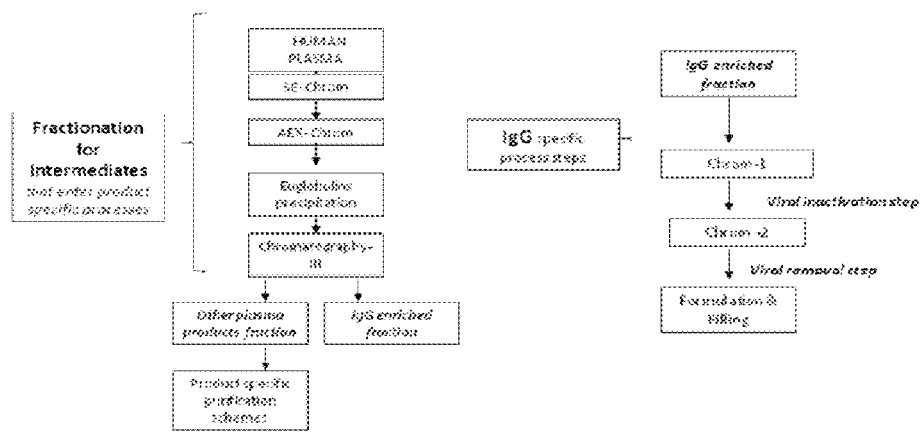
FIG. 2. HPLC analysis of IVIG
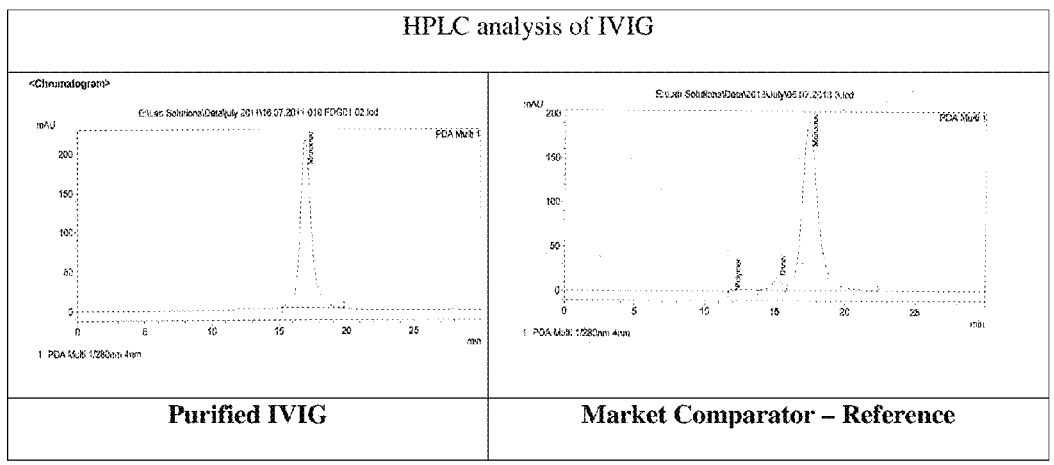

FIG. 3A. SDS-PAGE Analysis at different stages of purification

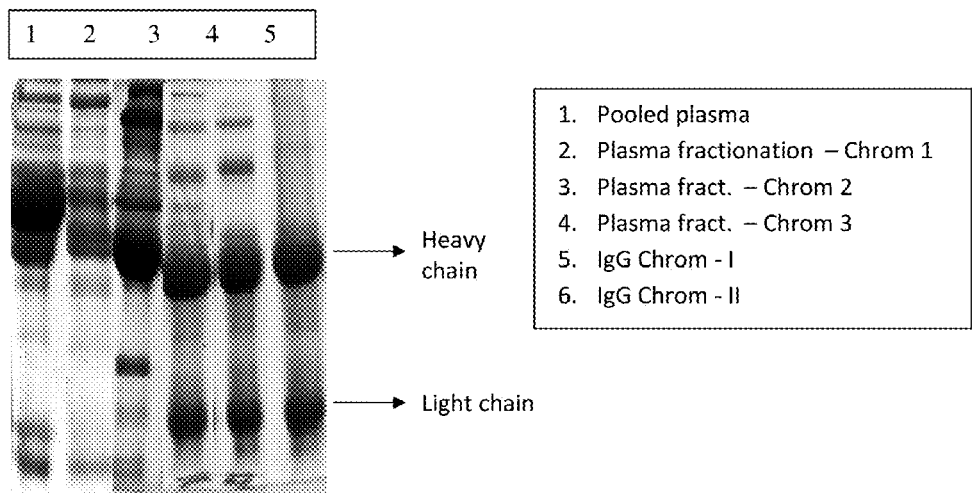

1. Pooled plasma
2. Plasma fractionation – Chrom 1
3. Plasma fract. – Chrom 2
4. Plasma fract. – Chrom 3
5. IgG Chrom - I
6. IgG Chrom - II

FIG. 3B. SDS-PAGE Analysis - Comparative analysis with a competitor brand (Reducing conditions)

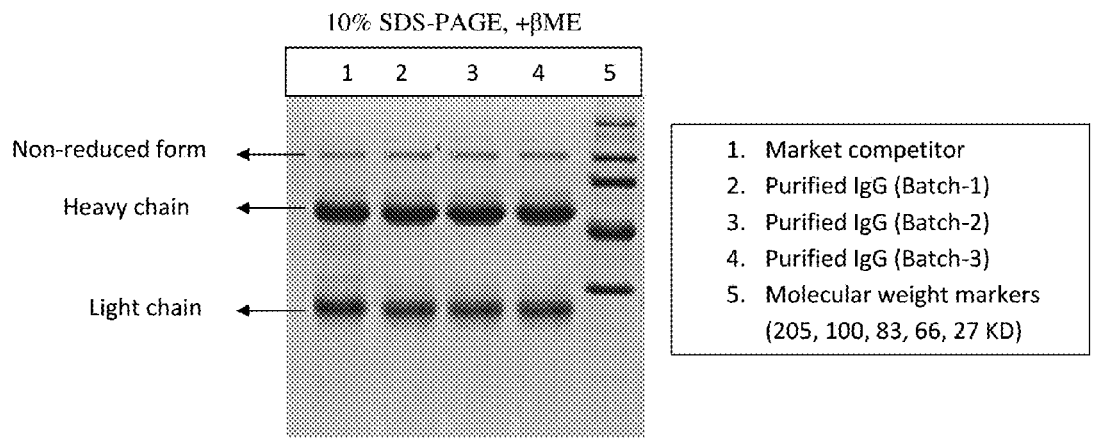

1. Market competitor
2. Purified IgG (Batch-1)
3. Purified IgG (Batch-2)
4. Purified IgG (Batch-3)
5. Molecular weight markers (205, 100, 83, 66, 27 KD)

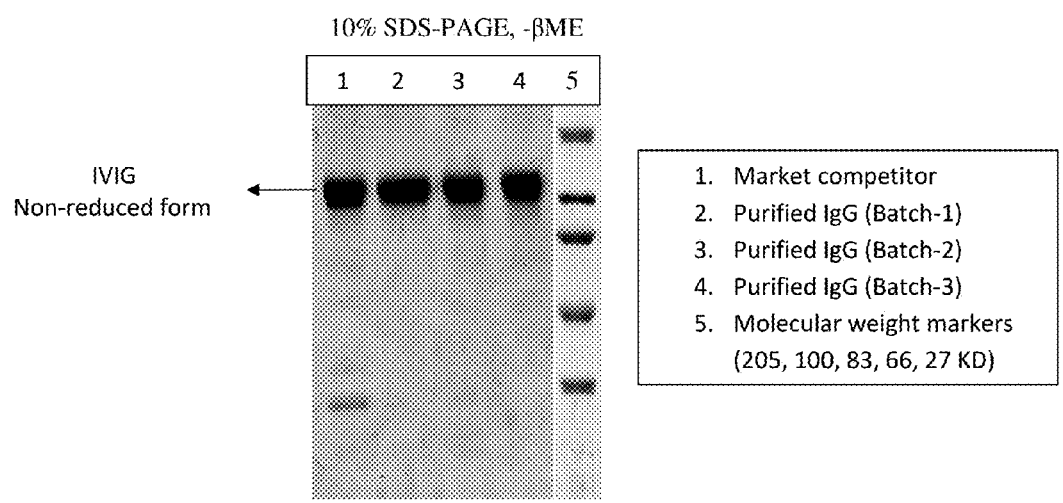
FIG. 3C. SDS-PAGE Analysis – Comparative analysis with a competitor brand (Non-reducing conditions)

FIG. 4A. Table 1A
Gamma Globulin levels in donor plasma samples

| Donor | Gamma globulin (gm/dl) in plasma from US donors | Gamma globulin (gm/dl) in plasma from India donors |
|---|---|---|
| 1 | 0.74 | 1.10 |
| 2 | 1.04 | 1.27 |
| 3 | 0.81 | 1.30 |
| 4 | 0.71 | 1.24 |
| 5 | 1.01 | 0.95 |
| 6 | 1.02 | 1.36 |
| 7 | 0.96 | 1.24 |
| 8 | 1.19 | 1.10 |
| 9 | 0.84 | 0.97 |
| 10 | 1.17 | 1.15 |
| 11 | 1.03 | 1.01 |
| 12 | 0.93 | 1.12 |
| 13 | 1.34 | 1.10 |
| 14 | 1.12 | 1.16 |
| 15 | 1.32 | 1.57 |
| 16 | 1.02 | 1.06 |
| 17 | 1.16 | 1.25 |
| 18 | 1.23 | 1.22 |
| 19 | 1.01 | 0.98 |
| 20 | 1.21 | 1.05 |
| Average | 1.04 | 1.16 |

FIG. 4B. Table 1B

Yield of IgG from different batches

| Yield after major steps of IVIG purification process | | | | |
|---|---|---|---|---|
| Steps | | Batch 1 (gm/L) | Batch 2 (gm/L) | Batch 3 (gm/L) |
| Plasma | Total Protein | 50 | 58 | 54 |
| | IgG | 11.16 | 10.60 | 11.20 |
| Plasma Fract - Chrom IV | Total Protein | 35.05 | 36.09 | 32.96 |
| | IgG | 9.63 | 8.99 | 9.83 |
| IgG – Chrom -I | Total Protein | 10.83 | 11.5 | 9.17 |
| | IgG | 8.83 | 8.0 | 8.17 |
| IgG – Chrom - II | Total Protein | 7.5 | 7.27 | 7.92 |
| | IgG | 7.5 | 7.27 | 7.92 |
| Final yield after formulation | Total Protein | 7.42 | 7.24 | 7.84 |
| | IgG | 7.42 | 7.24 | 7.84 |

FIG. 5. Table 2

Yield of IgG from 600 litre scale plasma batches

| Batches | Yield in gm/ litre of plasma | Total quantity of IVIG in Kgs |
|---|---|---|
| 1 | 7.46 | 4.47 |
| 2 | 7.29 | 4.37 |
| 3 | 7.63 | 4.57 |
| 4 | 7.08 | 4.24 |
| 5 | 7.14 | 4.28 |
| 6 | 7.08 | 4.24 |
| 7 | 7.24 | 4.34 |
| 8 | 7.74 | 4.64 |
| 9 | 7.18 | 4.30 |
| 10 | 7.42 | 4.45 |
| 11 | 7.24 | 4.34 |
| 12 | 7.84 | 4.70 |

FIG. 6. Table 3

IgG Subclass distribution for different batches

| IgG Subclasses | Specification | Market Comparator | Batch 1 | Batch 2 | Batch 3 |
|---|---|---|---|---|---|
| IgG1 | 63%-69 % | 61.9 | 66.70% | 66.84% | 67.99% |
| IgG2 | 23.8%-31% | 33.1 | 27.86% | 28.17% | 24.50% |
| IgG3 | 2.9%-5.8 % | 3.6 | 4.09% | 3.40% | 3.84% |
| IgG4 | 1.4%-2.9 % | 1.4 | 1.55% | 1.59% | 1.67% |

FIG. 7. Table 4

IgG – Process or source related impurities for different batches

| Test | Specification | Market Comparator-1 | Market Comparator-2 | Batch 1 | Batch 2 | Batch 3 |
|---|---|---|---|---|---|---|
| Prekallikrein activator IU/ml | < 35 IU/mL | <8.5 | Data unavailable | Below LLD < 1.88 IU/mL) | Below LLD <1.88 IU/mL | Below LLD < 1.88 IU/mL |
| Ig A mg/L | < 4 mg/L | <200mg/L | < 80mg/L | Below LLD (<3.125 µg/L) | Below LLD (<3.125 µg/L) | Below LLD (<3.125 µg/L) |
| Ig M mg/mL | < 0.1mg/ mL | 0.0391 mg/mL | Label claim - Traces of IgM | 0.000004 mg/mL | 0.000008 mg/mL | 0.000020 mg/mL |

PROCESS FOR INCREASED YIELD OF IMMUNOGLOBULIN FROM HUMAN PLASMA

FIELD OF THE INVENTION

The present invention relates to the field of biopharmaceuticals, especially relates to an improved process for the preparation of high yields of purified immunoglobulins (IgG) from human plasma and suitable for therapeutic administration.

BACKGROUND OF THE INVENTION

The global demand for plasma is mainly driven by the requirement for intravenous immunoglobulin (IVIG), the usage of which has grown significantly in different medical areas like neurology, rheumatology, nephrology, dermatology, oncology, infectious diseases, allergy and immunology. With markets projected to grow at 7% to 13% annually, between now and 2020, more IVIG will have to be manufactured to meet the growing demand. Plasma being a scarce and exclusive commodity, there is a continuous need to upgrade and optimize the fractionation processes to maximally utilize this valuable resource. By continuously refining the existing processes, improvements can be achieved by way of process efficiencies, quality of end products and manufacturing yields. In the case of IVIG, increased yields can lead to increased market availability of a product that is the key driver of the plasma fractionation industry.

Majority of the IVIG manufacturers still prefer the classical method of producing IVIG that employs ethanol fractionation at least for the initial steps in the manufacturing process, although chromatography methods are slowly gaining ground. Classical manufacturing processes of IVIG using ethanol precipitation and the new strategies that can increase the practicability and yield of IVIG have been discussed by Andrea Buchacher and Gunter Iberer in Biotechnol. J. 2006, 1, 148-163. The classical Cohn's process of ethanol precipitation (Cohn, E. J., Strong, L. E., Hughes, W. L., Mulford, D. J., Ashworth, J. N., Melin, M., Taylor, H., L.; J. Am. Chem. Soc., 1946, 68, 459-475) succeeds in enriching the five most abundant proteins in fractions I to V by sequential precipitation, by increasing the concentration of ethanol at each step. Fibrinogen is precipitated in fraction I, γ-globulins in fraction II, lipid bearing β-globulins in fraction III, α-globulins in fraction IV and albumin in fraction V. Fraction II and III is the starting material for most IVIG processes. In IVIG manufacture, most manufacturers commonly rely on the initial step of ethanol precipitation and fractionation of plasma, although the later steps may differ from manufacturer to manufacturer. Few continue with ethanol precipitation in the later steps of the process, whereas others may choose to use other precipitation methods like PEG or caprylate or even chromatography.

Although a few chromatography based processes have been described for the production of IVIG without the use of ethanol precipitation, but at the industrial scale, an all-chromatography process scheme has just begun gaining acceptance due to the better quality of the final IVIG product (lesser protein denaturation and aggregation) and better yields (Lontos, J., Chromatographic purification of immunoglobulins at CSL bioplasma; a manufacturing perspective. Plasma Product Biotech meet, 2005; Bertolini, J., Davies, J., Wu, J., Coppola, G., Purification of Immunoglobulins. 1998, WO 98/05686;

US2007049733 discloses ultra-high yield intravenous immune globulin preparation with the use of chromatographic methods in the final purification steps. The ethanol fractionation of plasma was replaced with caprylate or citrate precipitation steps followed by chromatography for purification. The final yields for most of these processes have been in the range of 4 to 6 gm per liter of plasma.

Most of Cohn's and modified Cohn's methods that are in use for the industrial production of IgG have reported yields in the range of 3.5 to 4.2 gm per liter of plasma. This is about 30 to 35% of the total IgG content (12 gm) in human plasma. As this is a high value product for the plasma product manufacturers, many major fractionators have been looking at improvements in their processes to increase yields, by shifting to chromatography based procedures. Substituting chromatography for traditional precipitation steps can not only help to increase yields but also provide a safer and better quality product for human administration.

EP0123029A1 discloses an improved process for the production of a solution of pure IgG-immunoglobulin fraction from natural plasma with unchanged complement-binding activity, which is in the form of a stable, clear aqueous solution for intravenous injection is available. Patent applications JPH09249580A, JPH107588A discloses a method of purification of a crude immunoglobulin-containing fraction and relates it to a process for the pharmaceutical preparation of intravenous immune for intravenous immunoglobulin for infusion using the same purified immunoglobulin. EP0180766, CN103554253, CN103665100, CN102552906, CN102584934 and JP2011102314 disclose processes for preparing human immunoglobulin for intravenous injection. EP2519540, U.S. Pat. No. 6,281,336B1 and CN104004089A disclose methods for producing intravenous human immunoglobulin.

U.S. Pat. No. 6,307,028 discloses a chromatographic method for high yield purification and viral inactivation of antibodies especially of the IgG type from human plasma and other sources.

The present invention discloses an approach to provide an ethanol-free high yielding method for recovering IgG from blood plasma and other blood based materials to the extent of 7 to 8 gm per liter of plasma which is better than the values reported so far in the plasma industry. Besides, the process described ensures that the other therapeutic proteins in the plasma are left untouched and available for extraction from the same plasma pool.

SUMMARY OF THE INVENTION

The present invention relates to an improved method to produce therapeutic grade immunoglobulins (IgG) in high yields from human plasma by a multi-step chromatography process that leaves the other therapeutic proteins in plasma still available for purification, by a separate set of product-specific chromatography steps. More particularly, the present invention relates to a method for ethanol-free separation of immunoglobulins from blood plasma or other blood based material by a process with high yields, in the range of 7 to 8 gm per liter which far exceeds the industry average of 3.5 to 4.2 gm per liter. In addition, the improved process manufactures IgG that is virally safe and of a far superior quality that is demonstrable by the low levels of impurities like product aggregates, pre-kallikrein activator, IgA and IgM levels. The distribution of various IgG isoforms (IgG$_1$, $IgG_2$, $IgG_3$, $IgG_4$) in the purified preparation closely matches the levels of IgG isoforms seen in human plasma.

BRIEF DESCRIPTION OF THE DRAWINGS

FIG. 1. An outline illustration of the process scheme for the purification of IgG.

FIG. 2. HPLC analysis of IVIG

FIG. 3A. SDS-PAGE Analysis at different stages of purification

FIG. 3B. SDS-PAGE Analysis—Comparative analysis with a competitor brand (Reducing conditions)

FIG. 3C. SDS-PAGE Analysis—Comparative analysis with a competitor brand (Non-reducing conditions)

BRIEF DESCRIPTION OF THE TABLES

FIG. 4A. Table 1A: Gamma Globulin levels in donor plasma samples

FIG. 4B. Table 1B: Yield of IgG from different batches

FIG. 5. Table 2: Yield of IgG from 600 liter scale plasma batches

FIG. 6. Table 3: IgG Subclass distribution for different batches

FIG. 7. Table 4: IgG—Process or source related impurities for different batches

DETAILED DESCRIPTION OF THE INVENTION

The present invention discloses a multi-step process that comprises of an initial fractionation of the human plasma into multiple fractions for further processing and by subjecting the fractions to a sequence of chromatography steps. The resulting IgG enriched fraction is further subjected to IgG-specific process steps for obtaining the final purified protein with high yields and therapeutic quality.

Fresh frozen plasma, recovered plasma or any other treated plasma fractions containing IgG collected from Indian blood banks is considered as the starting material. The plasma from individual donors is tested for absence of viruses like HIV-1 & 2, HBV and HCV. The gamma globulin levels in Indian plasma samples was found to have an average value of 1.16±20% gm/dl. This is not very different from the average gamma globulin levels reported in US plasma samples, which is around 1.04±20% gm/dl (Table 1A). The gamma globulin content in the plasma samples from India were estimated by nephelometry (an immunologically determined value based on antigen-antibody interactions) as a cumulative value of four sub-classes of IgG, ($IgG_1$, $IgG_2$, $IgG_3$, $IgG_4$). The gamma globulin levels in US plasma donors were determined by the serum plasma electrophoresis technique, by estimating the area for specific gamma globulin peak in the electropherogram. Both the techniques are quantitative, although the starting samples used in the estimation are different (blood plasma in India versus blood serum in US) and the estimates are comparable.

The present invention discloses a unique advanced chromatography-based production process that ensures a purified IgG yield of 7 to 8 gm per liter of plasma. The process ensures a recovery of 65 to 70% and hence a yield of greater than 7 gm per liter is achievable irrespective of the source of plasma used for fractionation and purification of IgG.

The detailed process for purification begins with the plasma bags that have been tested and certified free of viruses.

The pooled plasma is filtered to remove particulate matter, if any, followed by gel permeation column for the removal of high molecular weight lipids and lipoproteins while separating the protein fractions of interest. Further fractionation is achieved by removing euglobulins followed by filtration before they are loaded on capture chromatography resins, thereby minimizing fouling of the columns.

The protein fractions from the plasma fractionation process steps are fed into the subsequent process schemes for the purification of individual plasma proteins. The IgG enriched fractions are further purified by ion-exchange resins after the euglobulin removal step.

The present invention is illustrated through examples for better understanding and should be understood that they are not limiting and that variations can be made without departing from the scope and spirit of the invention.

Example 1

The thawed and pooled plasma fraction obtained from after filtration through a 45 microns filter is loaded onto a SE-chromatography column packed with a resin such as Sephacryl, Cellufine or other similar resins, although those skilled in the art will know that equivalent resins from other vendors may also be used to obtain similar outcomes. The column is run in a buffer composed of phosphate, citrate or similar buffer salts in the pH range of 6.0 and 7.5. The buffer salt molarity is in the range of 20 mM to 200 mM, preferably less than 150 mM. In addition, the buffer contains an additive such as NaCl in the range of 0.1M to 0.2M. The column is loaded with around 600 liters of thawed plasma and the fractions containing various plasma proteins including IgG are collected by running the column with about two to four column volumes of the buffer. By increasing the lot numbers, the batch size can be increased to 1200 liters or 2400 liters, for the same process.

The plasma fractions from the column containing non-IgG proteins are diverted to product-specific purification schemes at this stage. The plasma fraction containing IgG is subjected to further fractionation on a anion exchange (AEX) column chromatography step to separate out other therapeutic proteins that may be present along with IgG in this plasma fraction. The anion exchange chromatography step is equilibrated with acetate, citrate or any other anionic buffer salt of molarity 0.01M to 0.15M in the pH range 6.5 to 8.0 to primarily separate other therapeutic proteins from IgG, so that each of these proteins can be subjected to further processing and purification. The sample that is left unbound and contains the IgG enriched protein fraction is then subjected to a low pH precipitation step to remove the euglobulins contaminating the fraction. The euglobulin precipitation step is carried out preferably in the pH range of 4 to 7. The plasma sample is maintained under these conditions at a temperature ranging from 2 to 20 degrees centigrade, for a time of 2 hrs to 16 hrs. The euglobulin pellet obtained after continuous centrifugation has a weight of about 20-45 gm/L of plasma. The supernatant obtained after the euglobulin precipitation step is subjected to another anion exchange chromatography such as DEAE column to enable separation of IVIG from the other major plasma protein like albumin. The column has a height ranging from 5 and 25 cm and the column is equilibrated with a buffer made from salts like acetate, citrate or phosphate at concentration ranges from 5 mM to 100 mM in the pH range of 4.0 to 7.0. The flow through fraction containing enriched IgG (albumin depleted) is the starting sample for entering the IgG specific purification & polishing steps. The other major plasma proteins such as albumin and those retained through binding to the column are subjected to product-specific purification process steps.

The product-specific process for IgG purification (FIG. 1) begins from the above albumin depleted fraction as the starting material. This fraction comprises IgG but is depleted of albumin and several other therapeutic proteins from plasma, which have been diverted into individual product-specific purification pathways. The IgG containing protein fraction is then directed into a IgG-specific purification process comprising of loading the fraction onto an ion-exchange column such as Q-Sepharose (QAE, TMAE or other anionic resins from different vendors may also be substituted) to further purify the IgG to obtain >98% purity. The non-IgG proteins from the plasma that were co-purified till this step are removed by this column. The column packed with Q-sepharose or similar resins is equilibrated with acetate, citrate, phosphate or any other suitable buffer salt with a molarity ranging from 5 mM to 100 mM, more preferably ranging from 10 mM to 60 mM, and pH in the range of 5 to 8. The IgG containing fraction collected from this column is subjected to low pH treatment at pH 4.0, temperature of 37 degrees C. for 12-16 hrs for viral inactivation. This is followed by subjection to a solvent-detergent (S/D) treatment (1% Tri-n-butyl phosphate, TNBP and 1% Triton X-100) for virus inactivation of enveloped viruses at pH 4.0 and temperature of 30 degrees C. for 4 to 16 hrs. To remove the S/D chemicals and further purify IgG, the sample is loaded on a cation-exchange column such as CM, SP or equivalent). The column is equilibrated with buffers of acetate, citrate, phosphate or any other suitable buffer salt with a molarity ranging from 5 mM and 50 mM in the pH range of 3.5 to 6.0. The column is washed with buffer containing glycine with a molarity ranging from 0.05 to 0.25M and eluted with the same glycine containing buffer by adding sodium chloride with a molarity ranging from 0.1M to 0.5M. The column height is maintained in the range of 10 to 20 cm. This sample is passed through a nanofilter to remove viruses and a series of ultra-filtration and diafiltration steps are carried out to concentrate the sample and reduce the conductivity to match the requirement for the desired formulation. The purified IgG product at >99% purity is formulated, sterile filtered and filled in vials (the product purity after purification steps is shown in FIG. 2, 3A, 3B, 3C).

The present invention discloses a unique advanced chromatography-based production process that ensures a purified IgG yield of >7 gm per liter of plasma. The yields at different stages of purification (Table 1B) and the average yields of several batches taken at 600 liters scale of starting plasma volume are shown in Table 2. Total IgG quantitation is carried out by Double Antibody Sandwich ELISA technique. The immunoglobulins (IgG) present in plasma or purified IgG sample can be quantitated by this method. The IgG protein present in the sample reacts with the anti-IgG Fc antibodies which have been coated on the surface of polystyrene microtitre wells. The unbound serum proteins are removed by washing, and anti-IgG Fc antibodies conjugated with horseradish peroxidise (HRP) solution is added to the wells to form complexes with previously bound IgG with anti IgG Fc. Following another washing step, the enzyme bound to the immunosorbent is assayed by the addition of a chromogenic substrate (3,3',5,5'-tetramethylbenzidine i.e. TMB). The absorbance at 450 nm is measured to determine the concentration of IgG in test sample. The quantity of IgG in the test sample can be interpolated from the standard curve constructed from International reference standard of human IgG.

The IgG preparations are highly pure, functionally intact with normal IgG sub-class distribution (Table 3) and effector functions.

The manufacturing process of IgG described above doesn't compromise on the biological activity of the IgG molecules. They are highly pure, functionally intact with normal IgG sub-class distribution and effector functions. The preparations are also safe with regard to pathogen safety and product and process related impurities. For example, the protein composition, by Zone electrophoresis, expected as per pharmacopoeial guidelines is IgG>96% and other contaminant proteins <4%. But the protein composition (by Zone electrophoresis) of the present invention, is IgG=100% with 0% contaminant proteins. The distribution of isoforms IgG1 (63% to 69%), IgG2 (23% to 31%), IgG3 (2.9% to 5.8%), IgG4 (1.4% to 2.9%) is exactly within the specified limits for each form, matching the plasma distribution of isoforms. Some of the comparator products tested have one or more isoforms outside the specification range. These results are tabulated in Table 3A (IgG subclass distribution for different batches). Levels of process related contaminants are several fold lower than the specifications in the monographs compared to market comparators. For instance, prekallikrein activator (PKA) level is <1.88 IU/ml against a monograph specification limit of <35 IU/ml whereas the comparator products has PKA content of <8.5 IU/ml. The IgA levels in the purified preparation (as per this invention) is found to be below LLD (lower limit of detection) i.e. <3.125 ug/L when the pharmacopoeial limit is set at <4 mg/L, whereas in one market comparator the IgA content is found to be <200 mg/L and in another market product the content was <80 mg/L. Another source related impurity in IgG preparations is IgM, its limit is defined by pharmacopoeia as <0.1 mg/ml. The levels of IgM in different batches of the purified product as per the present invention ranged from 0.000004 mg/ml to 0.000020 mg/ml whereas, the IgM content in the competitor product is found to be 0.0391 mg/ml. These results are shown in Table 4 (IgG—Process or source related impurities for different batches). This demonstrates that the disclosed process for IgG preparation in the present invention are safe with regards to pathogen safety and product and process related impurities such as IgA, IgM and Pre-kallikrein activator levels.

The IgG purification scheme disclosed in the present invention consistently produces a yield that is greater than 7.0 gm per liter of plasma on an industrial scale. The use of chromatography steps ensures better removal of other plasma protein impurities in IgG and the avoidance of ethanol and salt precipitation steps minimizes aggregation and denaturation of IgG molecules produced by this process.

It is understood that the examples and embodiments described herein are for illustrative purposes only and that various modifications or changes in light thereof are to be included within the spirit and purview of this application and scope of the appended claims.

The invention claimed is:

1. A method for obtaining high yield therapeutic grade immunoglobulin (IgG) from human plasma, comprising the steps of:
   i) fractionating human plasma on a size exclusion column in citrate, phosphate or acetate buffer salt with a molarity in the range of 20 to 150 mM and a pH in the range of 6.0 to 7.5 and collecting the IgG containing fraction;

ii) loading the IgG containing fraction on an anion exchange column with citrate, phosphate or acetate buffer salt with a molarity in the range of 0.01M to 0.15M and a pH in the range of 6.5 to 8.0 to bind non-IgG plasma proteins and to collect the flow through fraction containing IgG for subjecting it to euglobulin precipitation at a pH in the range of 5.0 to 5.5 and 2 to 8 degrees C. for 4 to 16 hrs;

iii) loading the euglobulin depleted IgG containing fraction on an anion exchange column equilibrated with citrate, phosphate or acetate buffer salt with a molarity in the range of 5 mM and 100 mM and a pH in the range of 5 to 8 and collecting the IgG sample in the flow through fraction of the column; wherein the flow through fraction from the anion exchange column is subjected to viral inactivation by two sequential steps, comprising incubation at a pH of 4.0 and 37 degrees C. for 16 hours and followed by solvent-detergent treatment carried out using 1% Tri-n-butyl phosphate and 1% Triton X-100 solution, at a pH of 4.0 and 30 degrees C. for 4 to 16 hours; and iv) subjecting the viral inactivated sample to final purification by a cation exchange resin carried out in a citrate, phosphate or acetate buffer salt at a pH in the range of 3.5 to 6.0 and a molarity in the range of 5 to 50 mM and the elution with sodium chloride with a molarity in the range of 0.1M to 0.5M.

2. The method of claim 1, wherein the yield of IgG as quantitated by Double Antibody Sandwich ELISA method is in the range of 7 to 8 gm per liter of the plasma.

3. The method of claim 1, wherein the therapeutic grade IgG obtained has the distribution of isoforms IgG1 in the range of 63% to 69%, IgG2 in the range of 23% to 31%, IgG3 in the range of 2.9% to 5.8%, and IgG 4 in the range of 1.4% to 2.9%; and impurities of pre-kallikrein activator, IgA and IgM within the limits of less than 1.88 IU/ml, less than 3.125 ug/ml and 0.000004 mg/ml to 0.0001 mg/ml respectively.

* * * * *